(12) United States Patent
Yang

(10) Patent No.: US 12,728,197 B2
(45) Date of Patent: Sep. 8, 2026

(54) DRIVING STRUCTURE OF A DRUG INFUSION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 632 days.

(21) Appl. No.: 18/035,293

(22) PCT Filed: Dec. 4, 2020

(86) PCT No.: PCT/CN2020/133736

§ 371 (c)(1),
(2) Date: May 4, 2023

(87) PCT Pub. No.: WO2022/110269

PCT Pub. Date: Jun. 2, 2022

(65) Prior Publication Data

US 2024/0009385 A1 Jan. 11, 2024

(30) Foreign Application Priority Data

Nov. 27, 2020 (WO) ................ PCT/CN2020/132037

(51) Int. Cl.
*A61M 5/00* (2006.01)
*A61M 5/142* (2006.01)

(52) U.S. Cl.
CPC .... *A61M 5/14212* (2013.01); *A61M 5/14248* (2013.01); *A61M 2005/14208* (2013.01); *A61M 2205/82* (2013.01)

(58) Field of Classification Search
CPC .......... A61M 5/14212; A61M 5/14248; A61M 2005/14208; A61M 2205/82
See application file for complete search history.

(56) References Cited

U.S. PATENT DOCUMENTS 6,554,800 B1 * 4/2003 Nezhadian .......... A61M 5/1456 604/152
6,656,158 B2 * 12/2003 Mahoney ............ A61M 5/1452 604/151

(Continued)

FOREIGN PATENT DOCUMENTS

CN 103260678 8/2013
CN 106139311 11/2016

(Continued)

OTHER PUBLICATIONS

"International Search Report (Form PCT/ISA/210) of PCT/CN2020/133736", mailed on Aug. 26, 2021, pp. 1-3.

*Primary Examiner* — Zakaria Elahmadi
(74) *Attorney, Agent, or Firm* — JCIP GLOBAL INC.

(57) ABSTRACT

A driving structure of a drug infusion device, includes at least one driving unit and at least one driving wheel; a linear actuator connected with the driving unit; a switch unit electrically connected with the linear actuator; a power supply, the power supply, the switch unit and the linear actuator electrically connected to form a power supply circuit; and a program unit, including a timer electrically connected to the switch unit, when the timer works, the switch unit is closed to turn on the power supply circuit, and the linear actuator is powered; when the timer stops working, the switch unit is opened to disconnect the power supply circuit, and the linear actuator stops being powered, which makes the infusion device have multiple different infusion modes and improves user experience.

8 Claims, 2 Drawing Sheets

(56) References Cited

U.S. PATENT DOCUMENTS

| | | | | |
|---|---|---|---|---|
| 7,144,384 | B2 * | 12/2006 | Gorman | A61M 5/1452 604/151 |
| 8,172,811 | B2 * | 5/2012 | Roe | F03G 7/06143 74/25 |
| 8,535,268 | B2 * | 9/2013 | Auld | A61M 5/14546 604/151 |
| 12,102,792 | B2 * | 10/2024 | Yang | A61M 5/14236 |
| 2003/0199824 | A1 * | 10/2003 | Mahoney | A61M 5/1452 604/155 |
| 2004/0064088 | A1 * | 4/2004 | Gorman | A61M 5/1452 604/93.01 |
| 2004/0153032 | A1 * | 8/2004 | Garribotto | A61M 5/14248 604/131 |
| 2005/0238507 | A1 * | 10/2005 | Dilanni | F04B 9/08 417/415 |
| 2009/0012359 | A1 * | 1/2009 | Tanaka | A61B 1/00158 600/114 |
| 2012/0165734 | A1 * | 6/2012 | Auld | A61M 5/16877 604/151 |
| 2018/0126068 | A1 * | 5/2018 | Nazzaro | A61M 5/1452 |
| 2019/0117881 | A1 | 4/2019 | Yang | |
| 2022/0143304 | A1 * | 5/2022 | Yang | A61M 5/14248 |

FOREIGN PATENT DOCUMENTS

| | | |
|---|---|---|
| CN | 111939371 | 11/2020 |
| CN | 111939386 | 11/2020 |
| CN | 111939387 | 11/2020 |
| WO | 2020233128 | 11/2020 |

* cited by examiner

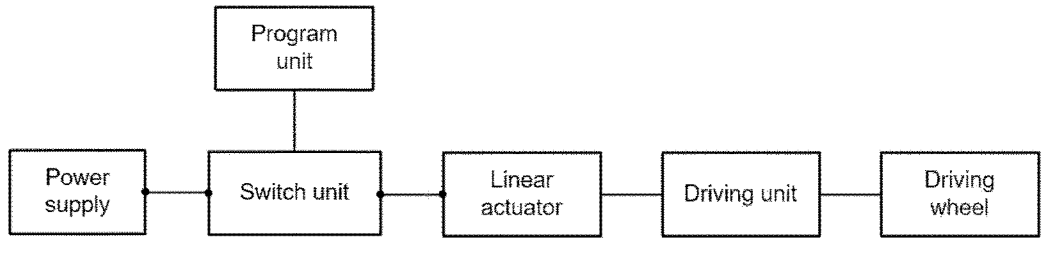
FIG.1
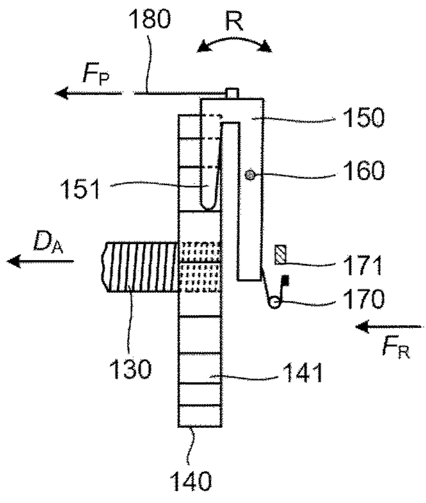
FIG.2
FIG.3

DRIVING STRUCTURE OF A DRUG INFUSION DEVICE

CROSS-REFERENCE TO RELATED APPLICATION

This application is a 371 application of the International PCT application serial no. PCT/CN2020/133736, filed on Dec. 4, 2020, which claims the priority benefit of the International PCT application no. PCT/CN2020/132037, filed on Nov. 27, 2020. The entirety of each of the above-mentioned patent applications is hereby incorporated by reference herein and made a part of this specification.

TECHNICAL FIELD

The present invention mainly relates to the field of medical instruments, in particular to a driving structure of a drug infusion device.

BACKGROUND

The pancreas in a normal person can automatically monitor the amount of glucose in the blood and automatically secrete the required dosage of insulin/glucagon. However, for diabetic patients, the function of the pancreas is abnormal, and the pancreas cannot normally secrete required dosage of insulin. Therefore, diabetes is a metabolic disease caused by abnormal pancreatic function and also a lifelong disease. At present, medical technology cannot cure diabetes, but can only control the onset and development of diabetes and its complications by stabilizing blood glucose.

Patients with diabetes need to check their blood glucose before injecting insulin into the body. At present, most of the detection methods can continuously detect blood glucose, and send the blood glucose data to the remote device in real time for the user to view. This detection method is called Continuous Glucose Monitoring (CGM), which requires the detection device to be attached to the surface of the patients' skin, and the sensor carried by the device is inserted into the subcutaneous tissue fluid for testing. According to the blood glucose (BG) level, the infusion device, as a closed-loop or semi-closed-loop artificial pancreas, injects the currently required insulin dose.

However, the current driving mode and infusion mode of the drug infusion device are relatively single, which worsens the user experience.

Therefore, the prior art urgently needs a drug infusion device with diversified infusion modes and better user experience.

BRIEF SUMMARY OF THE INVENTION

The embodiment of the present invention discloses a driving structure of a drug infusion device, a timer controls whether the linear actuator is powered, thus the driving unit has a variety of different movement modes, thereby making the infusion device have multiple different infusion modes, which improves user experience.

The invention discloses a driving structure of a drug infusion device, which comprises: at least one driving unit and at least one driving wheel, the driving unit, moving in the driving direction, can drive the driving wheel to rotate; a linear actuator connected with the driving unit; a switch unit electrically connected with the linear actuator; a power supply, the power supply, the switch unit and the linear actuator are electrically connected to form a power supply circuit that supplies power to the linear actuator, and the linear actuator pulling the driving unit to move in the driving direction after being powered; and a program unit, including a timer electrically connected to the switch unit, when the timer works, the switch unit is closed to turn on the power supply circuit, and the linear actuator is powered; when the timer stops working, the switch unit is open to disconnect the power supply circuit, and the linear actuator stops being powered.

According to one aspect of the present invention, the driving unit includes at least one driving portion, the driving wheel is provided with wheel teeth which can be pushed by the driving portion to drive the driving wheel.

According to one aspect of the present invention, the movement mode of the driving unit includes linear reciprocating movement or rotary reciprocating movement.

According to one aspect of the present invention, the driving unit includes two driving portions while the driving wheel includes two sub-wheels, and the two driving portions respectively cooperate with different sub-wheels, and the driving unit respectively drives different sub-wheels to rotate in two directions of the reciprocating rotation.

According to one aspect of the present invention, it also includes at least one blocking wall, and the driving unit reaches the movement end of the driving direction when contacts the blocking wall, and during the process of the driving unit moving in one entire driving direction, the movement time of the driving unit is t while the working time of the timer is T, then $T \geq t$.

According to one aspect of the present invention, 0 ms$\leq T-t \leq$30 ms.

According to one aspect of the present invention, it further includes an elastic member, and the reciprocating movement includes a driving direction and a resetting direction, and the elastic member applies a resetting and resilience force to the driving unit.

According to one aspect of the present invention, the switch unit includes a MOS field effect transistor, an analog switch or a relay.

According to one aspect of the present invention, the linear actuator is a shape memory alloy.

According to one aspect of the present invention, the driving unit includes a variety of different reciprocating frequencies, a variety of different reciprocating speeds, or a variety of different movement amplitudes.

Compared with the prior art, the technical solution of the present invention has the following advantages:

In the driving structure of the drug infusion device disclosed in the present invention, a program unit, including a timer electrically connected to the switch unit, when the timer works, the switch unit is closed to turn on the power supply circuit, and the linear actuator is powered; when the timer stops working, the switch unit is open to disconnect the power supply circuit, and the linear actuator stops being powered. The timer is used to control the switch unit to turn on or disconnect the power supply circuit, thereby controlling the power on and off of the linear actuator. Therefore, the user can adjust the driving mode of the driving unit as needed, such as the movement frequency or the movement amplitude of the driving unit, making the infusion device have more different infusion modes and improving user experience.

Furthermore, the driving unit includes two driving portions while the driving wheel includes two sub-wheels, and the two driving portions respectively cooperate with different sub-wheels, and the driving unit respectively drives different sub-wheels to rotate in two directions of the reciprocating rotation. The driving unit drives different sub-wheels to rotate in the two reciprocating directions respectively, which improves the infusion efficiency.

Furthermore, the elastic member applies a resetting and resilience force to the driving unit, making the driving unit move in the resetting direction. The elastic member can reset the driving unit automatically without consuming electric energy, which further reduces the power consumption of the infusion device.

BRIEF DESCRIPTION OF THE DRAWINGS

FIG. 1 is a schematic diagram of the connection relationship between the unit modules of the driving structure of a drug infusion device according to an embodiment of the present invention;

FIG. 2 is a partial schematic diagram of a driving structure providing with blocking wall according to an embodiment of the present invention;

FIG. 3 is a partial schematic diagram of a driving structure providing with blocking wall according to another embodiment of the present invention;

DETAILED DESCRIPTION

Figure 4A:
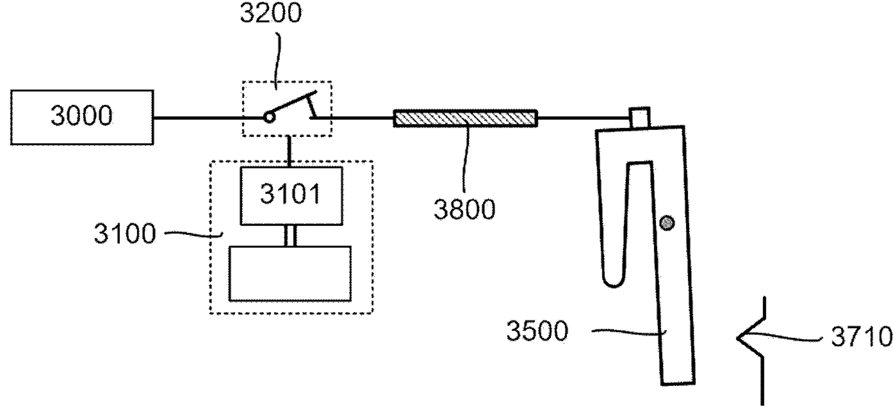
FIG. 4*a*-FIG. 4*c* are schematic diagrams of the control circuit of a driving structure according to another embodiment of the present invention.

As mentioned above, the driving mode and infusion mode of the drug infusion device in the prior art are relatively simple, worsening the user experience.

It is found through research that the cause of the above-mentioned problems is that the driving unit only has a fixed movement speed, movement amplitude, or movement frequency.

In order to solve this problem, the present invention provides a driving structure of a drug infusion device. A timer controls whether the linear actuator is powered or not. The driving unit has a variety of different movement modes, making the infusion device have a variety of different infusion modes, and improving user experience.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in following description of the drawings.

FIG. 1 is a schematic diagram of the connection relationship between the unit modules of the driving structure of the drug infusion device according to the embodiment of the present invention.

The drug infusion device includes an infusion needle, a drug storage unit, a piston arranged in the drug storage unit, a screw connected with the piston, a driving structure, and the like. The advancement of the screw can directly push the piston forward to achieve drug infusion.

The driving structure of the drug infusion device includes a power supply, a program unit, a switch unit, a linear actuator, at least one driving unit and at least one driving wheel.

The power supply is used to supply the power to the linear actuator. The linear actuator and the driving unit are connected to each other. The power supply, the switch unit and the linear actuator are electrically connected to form a power supply circuit for supplying the power to the linear actuator.

The program unit is used to control certain functional units in the infusion device to perform corresponding functions, such as including but not limited to controlling to open and close the switch unit, detecting the amount of the remaining drug, warning, and priming the infusion needle.

The switch unit is used to turn on or disconnect the power supply circuit that supplies power to the linear actuator, so as to control whether the linear actuator is powered. The switch unit includes MOS field effect transistor, an analog switch or a relay. Preferably, in the embodiment of the present invention, the switch unit is a MOS field effect transistor, which controls the conduction and disconnection of the channel according to the voltage change applied to the gate, thereby realizing the connection and disconnection of the power supply circuit.

The linear actuator is used to apply driving force to the driving unit for movement. When powered on, the physical form of the material of the linear actuator changes, which makes shrinkage deformation of the linear actuator occur, thereby exerting the driving force to move the driving unit. The higher the current is, the larger the shrinkage deformation of the linear actuator occurs, and the greater the driving force outputs. Obviously, when the current is constant, the driving force output by the linear actuator is also constant, because of which the linear actuator can output stable and controllable infusion driving force. Obviously, in the embodiment of the present invention, the higher the current is, the faster the driving unit moves; the longer the power-on time is, the greater the amplitude of the driving unit's movement is; and the greater the frequency of alternate power-on and power-off is, the greater the frequency of the driving unit reciprocates. Therefore, the infusion device has multiple different infusion modes, such as different infusion rates or different infusion increments, which will be described below.

Preferably, the linear actuator is an electrically driven linear actuator or an electrically heated linear actuator. By alternately being powered on and off, the linear actuator outputs power in pulses. Preferably, in the embodiment of the present invention, the linear actuator is a shape memory alloy.

The driving unit can drive the driving wheel to rotate, thereby realizing drug infusion. In the embodiment of the present invention, the driving unit includes at least one driving portion (like 151 in FIG. 2), and wheel teeth are provided on the driving wheel. Therefore, the driving portion can push the wheel teeth to drive the driving wheel to rotate, thereby driving the screw to advance. Preferably, in the embodiment of the present invention, a driving portion is provided on the driving unit, and the driving wheel is a ratchet wheel with ratchet teeth. The ratchet teeth can be pushed more easily, improving driving efficiency.

The movement mode of the driving unit includes linear reciprocating movement or rotary reciprocating movement. Preferably, in the embodiment of the present invention, the driving unit rotates reciprocating around a fixed shaft. The driving structure is also provided with an elastic member (like 170 in FIG. 2) for applying a resetting and resilience force to the driving unit. When the driving unit moves in the driving direction, the elastic member exerts an ever-increasing resetting and resilience force to the driving unit. The elastic member can reset the driving unit automatically without consuming electric energy which reduces the power consumption of the infusion device. Preferably, the elastic member is a spring.

Under the cooperation of the elastic member and the linear actuator, the driving unit performs a rotary reciprocating movement. And the driving unit can push the wheel teeth when it moves in the driving direction, and it stops pushing the wheel teeth while moving in the resetting direction, which will be described in detail below in conjunction with FIG. 2.

In other embodiments of the present invention, the driving unit may further include two or more driving portions while the driving wheel includes two or more sub-wheels, and different driving portions can be driven in cooperation with different sub-wheels. At this time, the linear actuator can pull the driving unit to push the wheel teeth in the two directions of reciprocating rotation respectively, making the driving wheel rotate. Therefore, there is no need to provide an elastic member.

In other embodiments of the present invention, the driving unit may also be a gear cooperating with the driving wheel, which is not specifically limited herein.

Generally, after moving for a certain distance, the driving unit needs to stop moving. Therefore, in order to determine the end point of the movement of the driving unit in the driving direction, the program unit is provided with a timer, which is electrically connected to the switch unit and controls the opening and closing of the switch unit. When the timer works, the switch unit is closed to turn on the power supply circuit, the linear actuator is powered, thus the driving unit moves in the driving direction. When the timer stops working, the switch unit is open to disconnect the power supply circuit, the linear actuator stops being powered, thus the driving unit stops moving in the driving direction, that is, reaching the movement end of the driving direction. Preferably, in the embodiment of the present invention, if the working duration of the timer is T, that is, the duration of the linear actuator powered is T.

In other embodiments of the present invention, the driving structure further includes a blocking wall which is used to determine the movement end of the driving unit in the driving direction, that is, when the driving unit contacts the blocking wall, the driving unit reaches the movement end in the driving direction, which will be described below.

Preferably, in the embodiment of the present invention, after a blocking wall is provided in the driving structure, if time of the driving unit rotating in the driving direction from the beginning to the contact with the blocking wall is t, then generally, $T \geq t$. That is, when the driving unit contacts the blocking wall, the timer immediately stops timing, or continues to count the time $T-t$. Obviously, the shorter the $T-t$ time is, the shorter time the linear actuator is powered, thus the lower the power consumption of the infusion device is. At the same time, this also reduces the time duration that the linear actuator is powered, effectively reducing the possibility of fatigue fracture of the linear actuator, and improving the reliability of the infusion device. Preferably, 0 ms$\leq T-t \leq$30 ms. In one embodiment of the present invention, $T-t$=5 ms. In still another embodiment of the present invention, $T-t$=10 ms. In yet another embodiment of the present invention, $T-t$=25 ms.

It should be noted that in the embodiment of the present invention, the driving unit includes multiple different movement modes, such as different movement speeds, different movement frequencies, or different movement amplitudes. For example, in an embodiment of the present invention, although the driving structure is provided with blocking wall, the infusion device can change the infusion mode according to the actual infusion demand, and the working time T of the timer is not long enough to make the driving unit contact the blocking wall, that is, the movement and stopping of the driving unit in the driving direction are completely controlled by the timer.

FIG. 2 is a partial schematic diagram of a driving structure providing with blocking wall according to an embodiment of the present invention.

In the embodiment of the present invention, when the linear actuator 180 pulls the driving unit 150 by force $F_P$, the driving unit 150 rotates counter-clockwise around the rotating shaft 160 to push the wheel teeth 141 forward to drive the driving wheel 140 rotate, thereby driving the screw 130 to advance in the D A direction. At this time, the elastic member 170 generates an ever-increasing resetting and resilience force $F_R$. The driving structure is also provided with a blocking wall 171 for determining the movement end point of the driving unit 150 in the driving direction. After contacting the blocking wall 171, the driving unit 150 stops moving in the driving direction. When the timer stops working, the driving unit 150 resets and rotates clockwise around the shaft 160 under the action of the elastic force $F_R$.

FIG. 3 is a partial schematic diagram of a driving structure providing with blocking wall according to another embodiment of the present invention.

The linear actuator 280 and the elastic member 270 act on the driving unit 250 with the force $F_P$ and $F_R$, respectively, making the driving unit 250 linearly reciprocate in the L direction. Therefore, the driving unit 250 can push the wheel teeth 241 in the driving direction, making the driving wheel 240 move in W direction to realize drug infusion.

Similarly, a blocking wall 271 is provided in the driving structure. After moving in the linear driving direction and contacting the blocking wall 271, the driving unit 250 stops. When the timer stops working, the driving unit 250 resets under the force of the elastic member 270. The driving principle is similar to the foregoing said, which will not repeat herein.

Hereinafter, the circuit control principle of the driving structure will be described by taking the rotating reciprocating movement of the driving unit as an example.

Figure 4B:
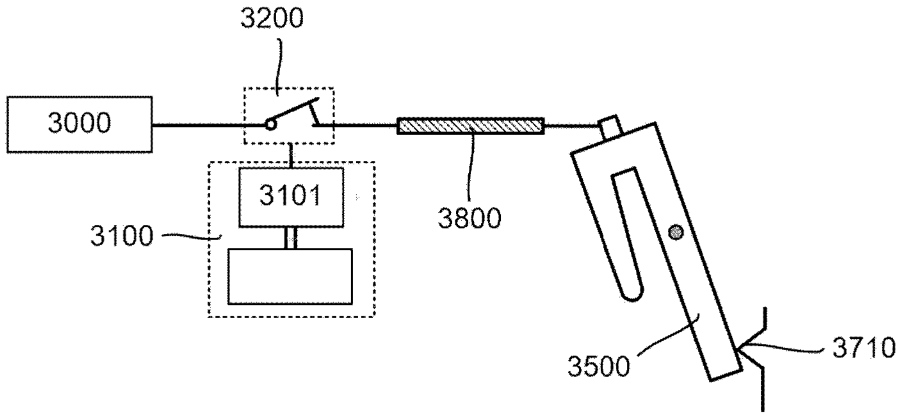
Figure 4C:
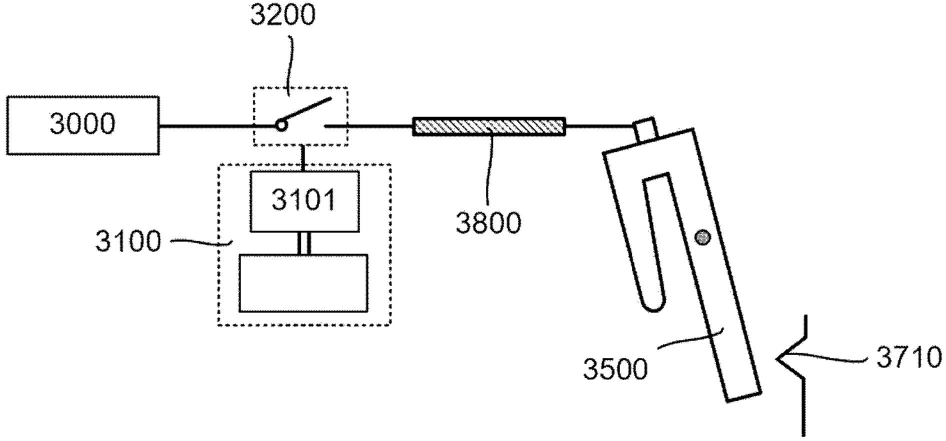

FIG. 4*a*-FIG. 4*c* are schematic diagrams of a driving structure control circuit according to an embodiment of the present invention.

As shown in FIG. 4*a*, in the embodiment of the present invention, the power supply 3000, the switch unit 3200 and the linear actuator 3800 are electrically connected to form a power supply circuit for supplying power to the linear actuator 3800. The embodiment of the present invention is provided with a blocking wall 3710. The program unit 3100 includes a timer 3101 for controlling the opening and closing of the switch unit 3200, thereby controlling the turning on and disconnection of the power supply circuit.

When the timer 3101 starts to work, the timing starts, and the switch unit 3200 is closed, making the linear actuator 3800 powered, thus the driving unit 3500 is pulled to start moving in the driving direction until the it contacts the blocking wall 3710, and the driving unit 3500 reaches the movement end in the driving direction. The time of the driving unit 3500 moving in the driving direction is t. After the driving unit 3500 contacts the blocking wall 3710, the timer 3101 continues to work until the working time reaches T, as shown in FIG. 4*b*. The timer 3101 controls to open the switch unit 3200, making the linear actuator 3800 stopped from supplying power. Subsequently, under the elastic member (not shown in FIG. 4*a*-FIG. 4*c*), the driving unit 3500 moves in the resetting direction, as shown in FIG. 4*c*.

In summary, the present invention discloses a driving structure of a drug infusion device. The timer controls whether the linear actuator is powered, thus the driving unit has a variety of different movement modes, thereby making the infusion device have multiple different infusion modes, which improves user experience.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A drive structure of a drug infusion device, comprising:

at least one driving unit and at least one driving wheel, wherein the driving unit, moving in a driving direction, drives the driving wheel to rotate;

a linear actuator connected with the driving unit;

a switch unit electrically connected with the linear actuator;

a power supply, wherein the power supply, the switch unit and the linear actuator are electrically connected to form a power supply circuit that supplies power to the linear actuator, and the linear actuator pulls the driving unit to move in the driving direction after being powered;

a program unit, including a timer electrically connected to the switch unit, when the timer works, the switch unit is closed to turn on the power supply circuit, and the linear actuator is powered;

when the timer stops working, the switch unit is opened to disconnect the power supply circuit, and the linear actuator stops being powered; and at least one blocking wall, wherein the driving unit reaches a movement end of the driving direction when contacting the at least one blocking wall, and during a process of the driving unit moving in the driving direction to contact the at least one blocking wall, a movement time of the driving unit is t while a working time of the timer is T, then T≥t, wherein when the working time of the timer reaches T, the switch unit is opened to disconnect the power supply circuit, and the linear actuator stops being powered.

2. The drive structure of the drug infusion device of claim 1, wherein the driving unit includes at least one driving portion, the driving wheel is provided with wheel teeth which are pushed by the driving portion to drive the driving wheel.

3. The drive structure of the drug infusion device of claim 2, wherein a movement mode of the driving unit includes a linear reciprocating movement or a rotary reciprocating movement.

4. The drive structure of the drug infusion device of claim 1, wherein $$0\text{ ms} \leq T - t \leq 30\text{ ms}.$$

5. The drive structure of the drug infusion device of claim 1, further comprising an elastic member, and a reciprocating movement includes the driving direction and a resetting direction, and the elastic member applies a resetting and resilience force to the driving unit.

6. The drive structure of the drug infusion device of claim 1, wherein the switch unit includes a MOS field effect transistor, an analog switch or a relay.

7. The drive structure of the drug infusion device of claim 1, wherein the linear actuator is a shape memory alloy.

8. The drive structure of the drug infusion device of claim 3, wherein the driving unit includes a variety of different reciprocating frequencies, a variety of different reciprocating speeds, or a variety of different movement amplitudes.

* * * * *